United States Patent [19]

Kuhn

[11] Patent Number: 5,040,979

[45] Date of Patent: Aug. 20, 1991

[54] DENTAL HANDPIECE WITH REMOVABLE HANDPIECE SLEEVE

[75] Inventor: Bernhard Kuhn, Schemmerhofen, Fed. Rep. of Germany

[73] Assignee: Kaltenbach & Voigt GmbH & Co., Biberach/Riss, Fed. Rep. of Germany

[21] Appl. No.: 558,786

[22] Filed: Jul. 26, 1990

[30] Foreign Application Priority Data

Aug. 25, 1989 [DE] Fed. Rep. of Germany ....... 3928210

[51] Int. Cl.$^5$ ............................................... A61C 1/08
[52] U.S. Cl. .................................................... 433/126
[58] Field of Search ......................... 433/126, 127, 128

[56] References Cited

U.S. PATENT DOCUMENTS

| 583,625 | 6/1897 | Lusby et al. | 433/128 X |
| 1,205,553 | 11/1916 | Lyon | 433/126 X |
| 2,376,294 | 5/1945 | Wahlberg | 433/126 |
| 2,376,295 | 5/1945 | Wahlberg | 433/126 |
| 2,876,015 | 3/1959 | Steuer et al. | 433/162 X |
| 3,475,817 | 11/1969 | Loge | 433/126 X |
| 3,631,597 | 1/1972 | Lieb et al. | 433/126 X |

FOREIGN PATENT DOCUMENTS

| 463543 | 3/1927 | Fed. Rep. of Germany | 433/127 |
| 565506 | 12/1930 | Fed. Rep. of Germany | 433/127 |
| 624716 | 5/1933 | Fed. Rep. of Germany | 433/127 |
| 2718750 | 11/1978 | Fed. Rep. of Germany | 433/127 |
| 3402585 | 8/1985 | Fed. Rep. of Germany | 433/126 |

*Primary Examiner*—Robert P. Swiatek
*Assistant Examiner*—Nicholas D. Lucchesi
*Attorney, Agent, or Firm*—Scully, Scott, Murphy & Presser

[57] ABSTRACT

A handpiece with a removable handpiece sleeve for worktools or dental implements which are releasably insertable therein with the assistance of a collet which is rotatable through the intermediary of a drive shaft. The collet is conically configured on its exterior at the thereof facing towards the dental implement and cooperates with the end correspondingly conically configured end of a spindle sleeve facing towards the implement, and in which the contact between the two conically-configured ends facing towards the implement is produced by a spring which is inserted intermediate an annular shoulder on the spindle sleeve and a clamping sleeve, and wherein the collet is releasable through a twisting turning motion imparted to the handpiece sleeve.

6 Claims, 3 Drawing Sheets

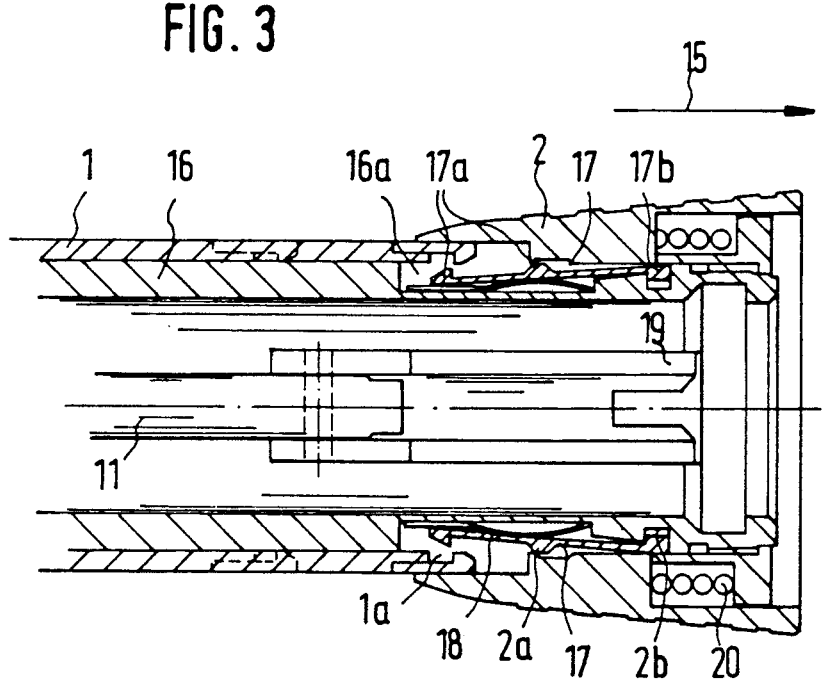

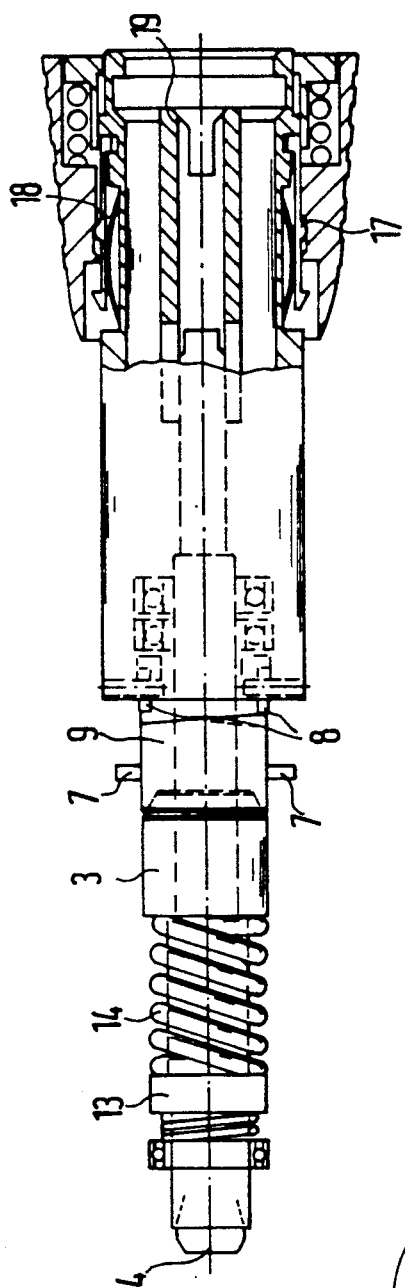
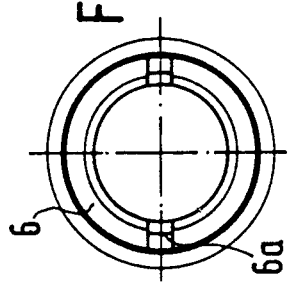
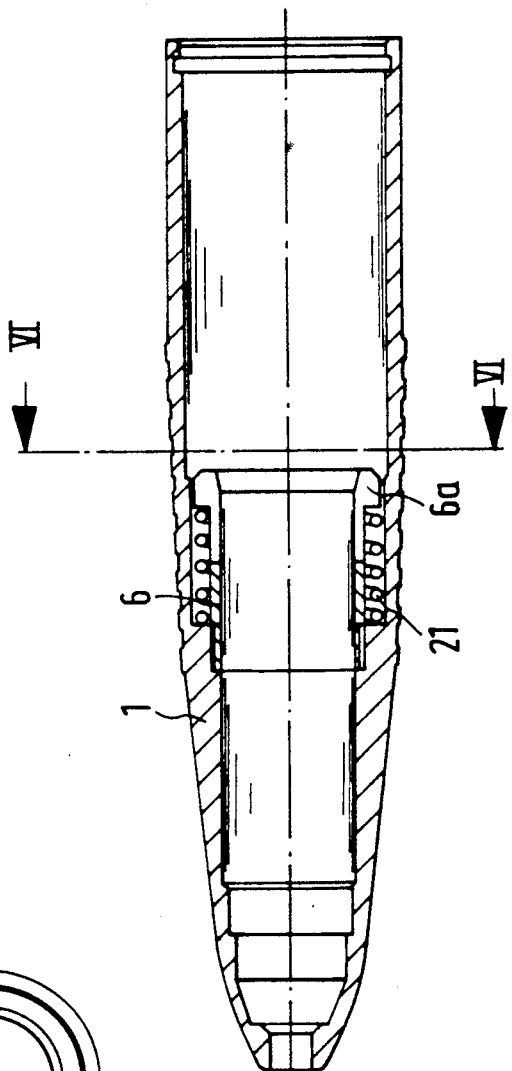

DENTAL HANDPIECE WITH REMOVABLE HANDPIECE SLEEVE

BACKGROUND OF THE INVENTION

1. Field of the Invention

The present invention relates to a handpiece with a removable handpiece sleeve for worktools or dental implements which are releasably insertable therein with the assistance of a collet which is rotatable through the intermediary of a drive shaft, wherein the collet is conically configured on its exterior at the end thereof facing towards the dental implement and cooperates with the end correspondingly conically configured of a spindle sleeve facing towards the implement, and in which the contact between the two conically-configured ends facing towards the implement is produced by means of a spring which is inserted intermediate an annular shoulder on the spindle sleeve and a clamping sleeve, and wherein the collet is releasable through a twisting turning imparted to the handpiece sleeve.

2. Discussion of the Prior Art

A handpiece of that type is essentially known from the disclosure of German Laid-Open Patent Appln. 22 34 231. In that particular instance, the inventive concept contemplates that for affording an easy handling or action during the actuation of a threaded sleeve for the formation of and elimination of a spring tension for effectuating the clamping of the implement, screwthread-like grooves are formed in the threaded sleeve and in the inner wall of an internal sleeve of the handpiece, and whereby suitable roll bodies are inserted into the grooves.

This prior art construction is encumbered by a plurality of disadvantages. On the one hand, the two screwthread-like grooves and the insertion of roll bodies entails a significant increase in the costs of manufacture and in the assembling of parts. Furthermore, the clamping force or; in essence, adjusting force can only be applied from one side, with the consequence of resulting in a poor centering of the dental implement. Because of the principle of utilizing a screwthread, notwithstanding the employment of roll bodies, the actuation is difficult in its handling, especially in such instances when it is impossible to prevent the ingress or penetrating of dirt. Moreover, there can also be encountered an automatic or spontaneous locking action, as a result of which the implement is retained in position at only a low or inadequate amount of force.

SUMMARY OF THE INVENTION

The present invention accordingly contemplates the provision of a dental handpiece of the type described hereinabove in which a rotatable pressure sleeve is arranged within the handpiece sleeve and which contacts against the clamping sleeve, and having formed thereon preferably two inclined o tapered rolling surfaces with which there cooperate one or more pressure rollers. This construction will enable that, upon a turning of the handpiece sleeve and of the pressure rollers, the pressure sleeve will axially move to such an extent under the pressure of the spring, as to eliminate or at least reduce the spring pressure to such an extent to thereby cause the release of the connection between the conical ends of the collet and of the spindle sleeve facing towards the dental implement.

Hereby, an object of the invention resides in the provision of such a handpiece incorporating a collet which ensures a good centering and thereby affords a dependable true running or rotation of the implement, a low-friction, simplified clamping and releasing of the collet, and guaranteeing a manipulation and operation of the handpiece and dental implement with a reliably closed collet.

The advantages of the invention can be readily ascertained in a correctly centered clamping for the worktool or dental implement, assured true running rotation of the implement, easy handling, simple construction for the clamping mechanism, and assuming operation of the handpiece with dependable clamping action, as a result of which there is eliminated the potential danger of injuries being sustained by the dentist due to a loosening implement. The entire arrangement is hereby simple and inexpensive to manufacture and during its installation. Moreover, the effective clamping force can be significantly increased.

BRIEF DESCRIPTION OF THE DRAWINGS

Further features of the invention may now be more readily ascertained from the following detailed description of an exemplary embodiment thereof, taken in conjunction with the accompanying drawings; in which:

FIG. 3 illustrates, on an enlarged scale, a sectional view through a detail of the handpiece;

FIG. 4 illustrates a longitudinal view, shown partly in section, of internal components of the handpiece constructed pursuant to the invention;

FIG. 5 illustrates the end of the handpiece facing towards the dental implement, with the omission of a number of detail parts; and FIG. 6 illustrates a sectional view perpendicular to the longitudinal axis, taken along line VI—VI in FIG. 5.

DETAILED DESCRIPTION

Figure 1:
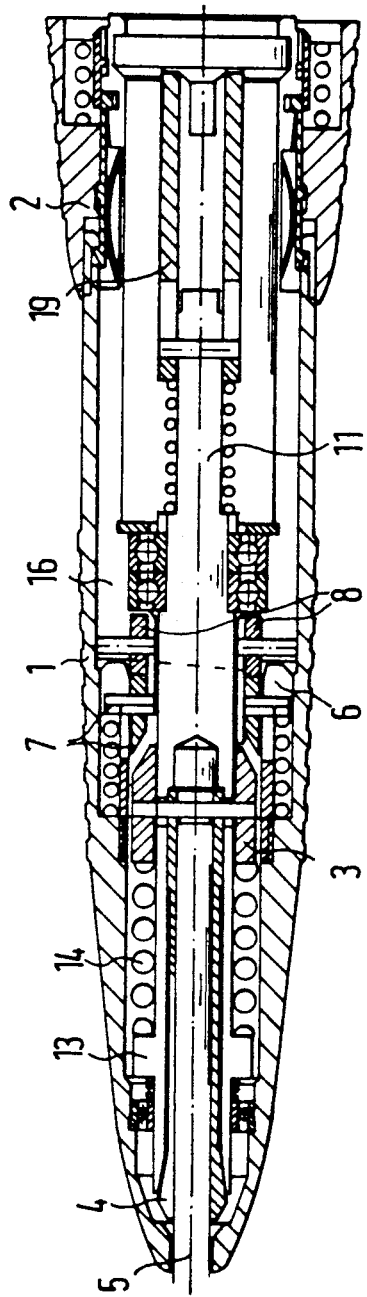
FIG. 1 illustrates a longitudinal sectional view through a handpiece constructed pursuant to the invention.

The handpiece, in its exterior construction, consists of a single-piece or unitary handpiece sleeve 1 which is axially inserted into an actuating sleeve 2. Reference numeral 3 identifies a clamping sleeve which, by means of a cross pin, is connected with a spindle sleeve 13, whose end facing towards the dental implement is interiorly conically tapered. A collet 4, whose end facing towards the dental implement is conformingly tapered, cooperates therewith so as to retain the implement in a load-transmissive connection. Arranged within the collet 4 is the worktool implement shaft 5, which leads to the dental implement (not shown). Reference numeral 6 designates a positioning or locating sleeve, which includes at least two radially outwardly extending positioning pins 7. Reference numeral 8 identifies pressure rollers which can inventively roll along a incline or tapered roll off surface 10 of a pressure sleeve 9. Preferably, two of such rolling surfaces 10 are provided.

The curved arrow 12 indicates the manner in which the handpiece sleeve 1 is to be turned relative to the actuating sleeve 2, in order to release the load-transmissive connection between both sleeves 1, 2.

Formed on the spindle sleeve 13 is an annular shoulder against which the spring 14 supports itself, which has the other end thereof contacting against the clamping sleeve 3, and which effectuates the contact between the two conically tapered ends of the parts 4 and 13 facing towards the implement; as a result of which the collet 4 is pressed inwardly against the implement shaft 5 and thus ensures the load-transmissive retention of the implement, which is so strong that the dental implement cannot be removed in a forward motion in this position, and also affords the transfer of the torque from the drive motor to the dental implement.

FIG. 3 illustrates the latching mechanism by means of which there is achieved the arresting or locking action between the two sleeves 1, 2 in the assembled condition thereof. Hereby, the arrow 15 indicates the manner in which the direction of movement of the handpiece sleeve 1 takes place with regard to the actuating sleeve 2 during assembly.

Inserted into the handpiece sleeve 1 is an inner sleeve 16 in a close fit therewith. This latter sleeve is provided at its right-hand end with an external annular groove 16a. Into this groove there are inserted the strip-shaped latching element 17, which are pressed outwardly through the intermediary of springs 18, preferably leaf springs. For the purpose of effectuating the arresting or latching action, the handpiece sleeve 1 is provided at its right-hand end with an internal annular groove 1a into which, subsequent to the sliding together of the sleeves 1, 2, there engages a projection 17a of the latching element 17. A second projection 17a of the same element engages into an internal annular groove 2a which is formed in the actuating sleeve 2. This sleeve is supported against the inner sleeve 16 by means of a setting spring 20.

The latching element 17 is secured against axial displacement in that inner projections 17b engage into an external annular groove which is formed in the inner sleeve 16. The projections are secured by means of the actuating sleeve 2 against their falling out, since the inner wall of the actuating sleeve 2 encompasses the inner sleeve 16.

Arranged on the shaft 7, which is positioned so as to extend coaxially with the implement shaft 5, is a follower 9 serving as a coupling element for providing the connection with the shaft of a driving motor (not shown).

In FIG. 5 there can be ascertained the positioning sleeve 6 which incorporates at least two axial or longitudinally extending slots 6a, into which there engage the positioning pins 7 of the pressure sleeve 9 in an axially displaceable manner.

The positioning sleeve 6 is supported against the handpiece sleeve 1 by means of a spring 21.

FIG. 3 illustrates the manner in which the handpiece sleeve 1 is inserted into the actuating sleeve 2. For this purpose, the sleeve 1 is inserted into the latter and axially displaced along the direction of arrow 15. Hereby, the right hand end of the handpiece sleeve 1 slides with a groove (not shown) formed therein past a forward projection 17a on the latching element 17, until the projection will engage under the pressure of its spring 18 into the annular groove 1a which is formed in the handpiece sleeve 1. Concurrently, the other projection 17a engages into the annular groove 2a formed in the actuating sleeve 2. Thereafter, the handpiece sleeve 1 is turned by a limited amount with respect to the actuating sleeve 2 opposite the direction of rotation 12. This has as a result that the forward projection 17a on the latching element 17 will exit from the region of the elongate groove, and upon the exertion of a pull opposite the direction 15, will position itself behind the right-hand end of the annular groove 1a and thereby counteract the tensile or pulling force of a load-transmissive contact. Thereby, in this position the two sleeves are secured through a bayonet-joint against axially directed separating forces.

Figure 2:
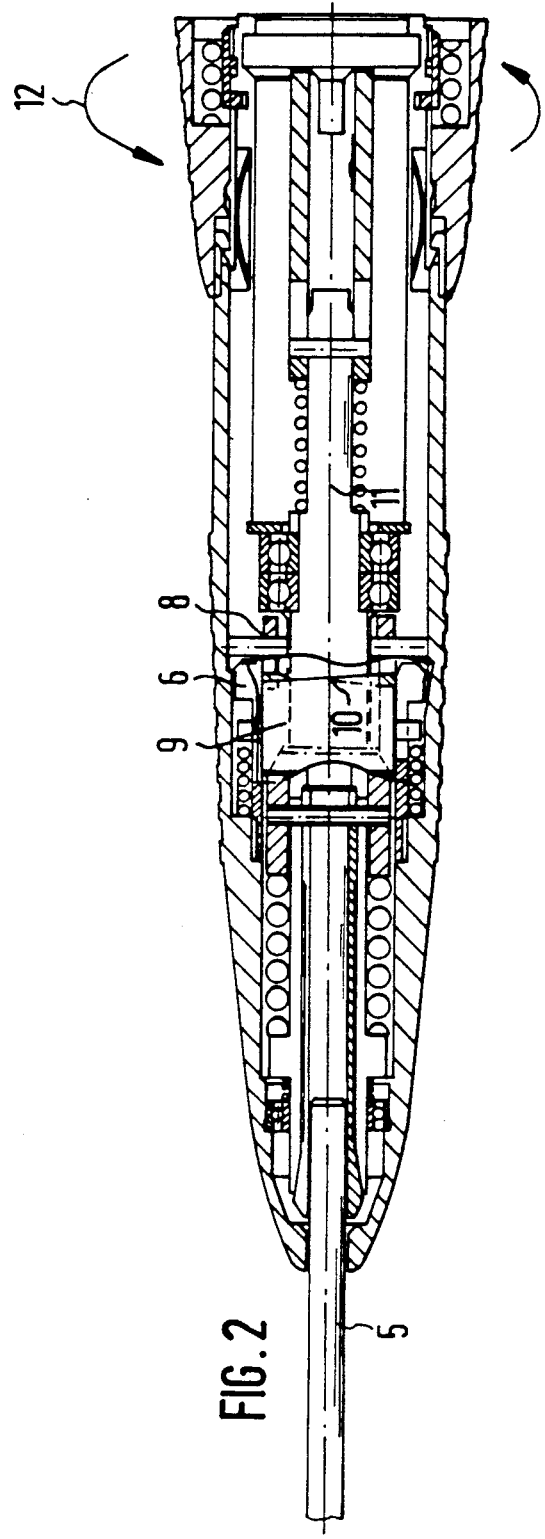
FIG. 2 illustrates a longitudinal sectional view similar to FIG. 1, wherein there is shown a side view of an internal detail.

For effecting the release of this connection, the handpiece sleeve 1 is initially turned bayonet-like relative to the actuating sleeve 2 in the sense or direction of the arrow 12 (FIG. 2). Thereafter, the two sleeves 1, 2 can be separated from each other opposite the direction of arrow 15 in the manner of a bayonet-joint.

Inventively, upon the turning the handpiece sleeve 1 there are concurrently turned therewith the pressure rollers. These roll down along the rolling surface 10 on the pressure sleeve 9. While, as illustrated in FIG. 2, the one of the two diametrically oppositely located pressure rollers 8 contact from below against the forward or leading edge of the rolling surface or plane 10, and as a result thereof, the pressure sleeve 9 and the clamping sleeve 3 contacting thereagainst are pressed towards the left, and thereby the spring 14 will tension such that the collet 4 is closed, upon a rotation or turning of the handpiece sleeve 1 in the direction of arrow 12 in conjunction with the taking along of the pressure rollers 8, the pressure sleeve 9 is displaced towards the right in response to the pressure of the spring 14, such that the pressure of the spring 14 is reduced by such an extent as to cause the release from the load-transmissive clamping restraint of the dental implement in the collet. The dental implement can thereafter be drawn out forwardly and removed, as is indicated in FIG. 2.

What is claimed is:

1. A dental handpiece including a removable handpiece sleeve for dental implements which are releasably insertable therein through the intermediary of a collet which is rotatable by a drive shaft, said collet being conically tapered on the exterior thereof at an end facing towards a retained dental implement and cooperating with a conformingly conically tapered end of a spindle sleeve; a spring effectuating contact between said conically-tapered ends facing the implement, said spring being inserted between an annular shoulder on the spindle and a clamping sleeve, said collet being releasable by imparting a turning movement to the handpiece sleeve; a rotatable pressure sleeve in said handpiece sleeve contacting said clamping sleeve, said pressure sleeve having two inclined rolling surfaces thereon, at least one pressure roller cooperating with said rolling surfaces such that upon rotation of the handpiece sleeve and of the at least one pressure roller the pressure sleeve axially displaces responsive tot he pressure of the spring such that the pressure of the spring is reduced to enable releasing the connection between the conical ends of the collet and of the spindle sleeve towards the dental implement.

2. A handpiece as claimed in claim 1, wherein there are provided two of said pressure rollers.

3. A handpiece as claimed in claim 2, wherein the pressure rollers are arranged diametrically opposite each other.

4. A handpiece as claimed in claim 1, wherein the turning of the handpiece sleeve releases a connection between said handpiece sleeve and an actuating sleeve, so as to enable said two sleeves to be separated from each other in response to an axial pull imparted thereto.

5. A handpiece as claimed in claim 4, wherein said connection comprises latching means including strip-shaped latching elements which engage with projections thereon into, respectively, an internal circumferential groove formed in the handpiece sleeve and in the actuating sleeve so as to be subjected an outwardly directed pressure of springs, comprising leaf springs, which are inserted into an external circumferential groove formed in an inner sleeve which is arranged within the handpiece sleeve.

6. A handpiece as claimed in claim 5, wherein the inner sleeve extends into the interior of the actuating sleeve in the assembled condition, and includes an external circumferential groove; and said latching elements include internal projections engaging into said external circumferential groove and are retained in this position by the inner wall of said actuating sleeve.

* * * * *